(12) United States Patent
Houck (10) Patent No.: US 12,048,080 B2
(45) Date of Patent: Jul. 23, 2024

(54) OPTICAL SYSTEM FOR FACILITATING OPTICAL DISINFECTION AND OPTICAL COMMUNICATION

(71) Applicant: VIAVI Solutions Inc., Chandler, AZ (US)

(72) Inventor: William D. Houck, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 88 days.

(21) Appl. No.: 17/816,830

(22) Filed: Aug. 2, 2022

(65) Prior Publication Data

US 2023/0042755 A1 Feb. 9, 2023

Related U.S. Application Data (60) Provisional application No. 63/228,928, filed on Aug. 3, 2021.

(51) Int. Cl.
*H05B 47/21* (2020.01)
*B08B 7/00* (2006.01)
*G02B 1/00* (2006.01)

(52) U.S. Cl.
CPC .......... *H05B 47/21* (2020.01); *B08B 7/0057* (2013.01); *G02B 1/002* (2013.01)

(58) Field of Classification Search
None
See application file for complete search history.

(56) References Cited

U.S. PATENT DOCUMENTS

| 2008/0118867 A1* | 5/2008 | Sato | G03F 7/0295 430/286.1 |
| 2012/0310141 A1* | 12/2012 | Kornfield | A61F 9/0008 604/20 |
| 2020/0200357 A1* | 6/2020 | Gray | F21V 5/008 |

FOREIGN PATENT DOCUMENTS

WO WO-2017174549 A1 * 10/2017

OTHER PUBLICATIONS

WO2017174549 translation (Year: 2023).*
E.A. Boardman, et al.; "Deep ultraviolet (UVC) laser for sterilisation and fluorescence applications"; Sep. 2012; pp. 31-35.

(Continued)

*Primary Examiner* — Eric W Golightly
(74) *Attorney, Agent, or Firm* — Harrity & Harrity, LLP (57) ABSTRACT

An optical system includes a plurality of laser light sources and an optical component. A first set of one or more laser light sources is configured to emit optical disinfection light at the optical component. A second set of one or more laser light sources is configured to emit optical communication light at the optical component. The optical component is configured to distribute the optical disinfection light in a first light distribution pattern, and to distribute the optical communication light in a second light distribution pattern. The optical component includes a first set of one or more metamaterial structures configured to distribute, in the first light distribution pattern, the optical disinfection light that is incident on the optical component, and a second set of one or more metamaterial structures configured to distribute, in the second light distribution pattern, the optical communication light that is incident on the optical component.

20 Claims, 6 Drawing Sheets

(56) References Cited

OTHER PUBLICATIONS

Norman Ruhnke; "A deep ultraviolet laser light source by frequency doubling of GaN based external cavity diode laser radiation"; Aug. 2020, 130 pages; Berlin, Germany.
Manuela Buonanno, et al.; "Far-UVC light (222 nm) efficiently and safely inactivates airborne human coronaviruses"; Scientific Reports; 2020; pp. 1-8; vol. 10:10285.

* cited by examiner

OPTICAL SYSTEM FOR FACILITATING OPTICAL DISINFECTION AND OPTICAL COMMUNICATION

CROSS-REFERENCE TO RELATED APPLICATION

This Patent application claims priority to U.S. Provisional Patent Application No. 63/228,928, filed on Aug. 3, 2021, and entitled "SYSTEM FOR BROAD AREA DISINFECTION AND WIRELESS COMMUNICATION." The disclosure of the prior Application is considered part of and is incorporated by reference into this Patent Application.

BACKGROUND

Ultraviolet-C (UVC) light, light associated with a spectral range of 200 to 280 nanometers (nm) (e.g., light with a wavelength that is greater than or equal to 200 nm and less than or equal to 280 nm), can be used for optical disinfection of air, surfaces, water, and other substances.

SUMMARY

In some implementations, an optical system includes a plurality of laser light sources; and an optical component, wherein: a first set of one or more laser light sources, of the plurality of laser light sources, is configured to emit optical disinfection light at the optical component, a second set of one or more laser light sources, of the plurality of laser light sources, is configured to emit optical communication light at the optical component, the optical component is configured to distribute the optical disinfection light in a first light distribution pattern, and the optical component is configured to distribute the optical communication light in a second light distribution pattern.

In some implementations, an optical system includes a plurality of laser light sources; and an optical component, wherein: a first set of one or more laser light sources, of the plurality of laser light sources, is configured to emit optical disinfection light at the optical component, a second set of one or more laser light sources, of the plurality of laser light sources, is configured to emit optical communication light at the optical component, the optical component is configured to distribute the optical disinfection light in a plurality of first light distribution patterns, and the optical component is configured to distribute the optical communication light in a plurality of second light distribution patterns.

In some implementations, an optical component includes a first set of one or more metamaterial structures disposed on at least one surface of the optical component; and a second set of one or more metamaterial structures disposed on the at least one surface of the optical component, wherein: the first set of one or more metamaterial structures are configured to distribute, in a first light distribution pattern, optical disinfection light that is incident on the optical component, and the second set of one or more metamaterial structures are configured to distribute, in a second light distribution pattern, optical communication light that is incident on the optical component.

DETAILED DESCRIPTION

The following detailed description of example implementations refers to the accompanying drawings. The same reference numbers in different drawings may identify the same or similar elements.

UVC light (e.g., light with a wavelength between 200 and 280 nm) is effective at disinfection of air, surfaces, water, and other substances (e.g., by killing bacteria, viruses, fungi, and/or other biological material). Further, Far UVC light (e.g., light with a wavelength between 207 and 222 nm) is effective at disinfection, and is considered safe for human tissue when radiant exposure associated with the Far UVC light is less than a radiant exposure threshold, such as 5 millijoules per square centimeter per hour ($mJ/cm^2/hr$). However, creating an optical system that provides UVC light, or Far UVC light, in a manner that enables proper disinfection and is energy efficient is difficult. For example, conventional light sources (e.g., LEDs or excimer lamps) that emit UVC light are only about 12% efficient.

Additionally, in some cases, it is desired provide wireless communications using light (e.g., using infrared (IR)), such as to reduce radiofrequency (RF) emissions within an area that is sensitive to RF emission. For example, it may be desirable to reduce RF emissions in an airport, hospital, or laboratory, to avoid potential negative impacts with sensitive electronic equipment. Further, communicating via light may enable providing higher data transmission rates (as compared to that provided by typical RF techniques). However, an optical system that provides "full coverage" wireless communication requires uniform (or near-uniform) illumination of a large area, such as a room of a building, to limit system complexity and to allow for unconstrained movement of user equipment (e.g., that are to communicate with the optical system) within the space.

Some implementations provide an optical system that includes a first set of laser light sources configured to emit optical disinfection light (e.g., UVC light or Far UVC light) at an optical component, and a second set of laser light sources configured to emit optical communication light 112 (e.g., infrared light, or any light that can be modulated to enable transmission of data) at the optical component. The optical component is a diffuser and/or includes one or more metamaterials to diffuse both the optical disinfection light 110 and the optical communication light 112. The optical component distributes the optical disinfection light in one or more first light distribution patterns and distributes the optical communication light in one or more second light distribution patterns. For example, the optical component includes a first set of one or more metamaterial structures configured to distribute, in the one or more first light distribution patterns, the optical disinfection light (e.g., that is incident on the optical component), and includes a second set of one or more metamaterial structures configured to distribute, in the one or more second light distribution patterns, the optical communication light (e.g., that is incident on the optical component).

In this way, the optical system enables efficient illumination of large volumes and areas for the purpose of both disinfection communication and wireless communication. Further, the optical system provides compactness, energy efficiency (e.g., because the optical system uses efficient laser sources, such as aluminum gallium nitride (AlGaN) laser light sources, that are greater than 12% efficient), and multi-functional performance. Moreover, a complexity of the optical system is reduced compared to a typical optical system that includes lamps with large reflectors that produce hot spots and other illumination challenges. No reflectors are needed for the optical system described herein. Additionally, the optical system provides light associated with different wavelength ranges, without a need to add a fully independent second optical system.

FIGS. 1A-1D are diagrams illustrating example implementations of an optical system 100. As shown in FIGS. 1A-1D, the optical system 100 may comprise a plurality of laser light sources 102, which may include a first set of one or more laser light sources 104 and/or a second set of one or more laser light sources 106, and/or an optical component 108.

The first set of one or more laser light sources 104 may include one or more laser light sources, such as AlGaN laser light sources, that are configured to emit optical disinfection light 110 (e.g., at the optical component 108). The optical disinfection light 110 may include UVC light (e.g., light associated with a spectral range of 200 to 280 nanometers), Far UVC light (e.g., light associated with a spectral of 207 to 222 nm), and/or another portion of UVC light. Accordingly, the optical disinfection light 110 may be capable of optically disinfecting (e.g., by sterilizing bacteria, viruses, fungi, and/or other biological material) air, a surface, water, and/or another object or substance.

The second set of one or more laser light sources 106 may include one or more laser light sources that are configured to emit optical communication light 112 (e.g., at the optical component 108). In some implementations, the optical communication light 112 may include non-UVC light (e.g., light not associated with a spectral range of 200 to 280 nanometers). For example, the optical communication light 112 may include visible light (e.g., light associated with a spectral range of 400 to 779 nm), near-infrared (NIR) light (e.g., light associated with a spectral range of 780 to 1399 nm), short-wavelength infrared (SWIR) light (e.g., light associated with a spectral range of 1400 nm to 2999 nm), mid-wavelength infrared (MWIR) light (e.g., light associated with a spectral range of 3000 to 7999 nm), and/or long-wavelength infrared (LWIR) light (e.g., light associated with a spectral range of 8000 to 15000 nm), among other examples. Additionally, or alternatively, the optical communication light 112 may include ultraviolet (UV) light (e.g., light associated with a spectral range of 100 to 399 nm), UVC light, Far UVC light, and/or another portion of the UV light. In some implementations, the optical system 100 may include and/or may be associated with a controller (not shown) that is configured to modulate respective intensities of the second set of one or more laser light sources 106. Accordingly, the optical communication light 112 may be capable of transmitting communication data to one or more communication devices that are configured to detect and process the optical communication light 112 (e.g., according to an optical communication technique, such as LiFi).

Figure 1A:
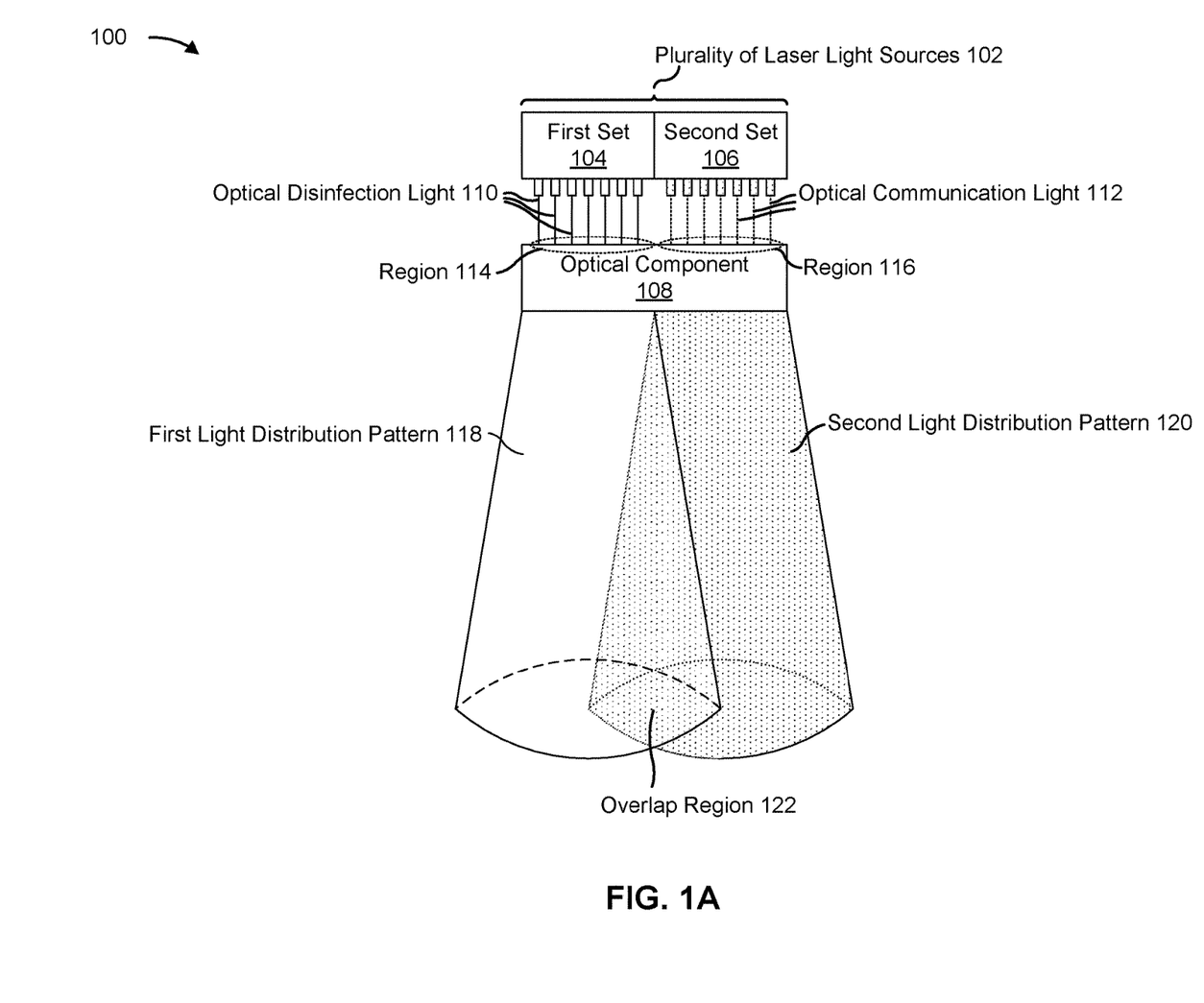
FIGS. 1A-1D are diagrams illustrating example implementations of an optical system described herein.
Figure 1B:
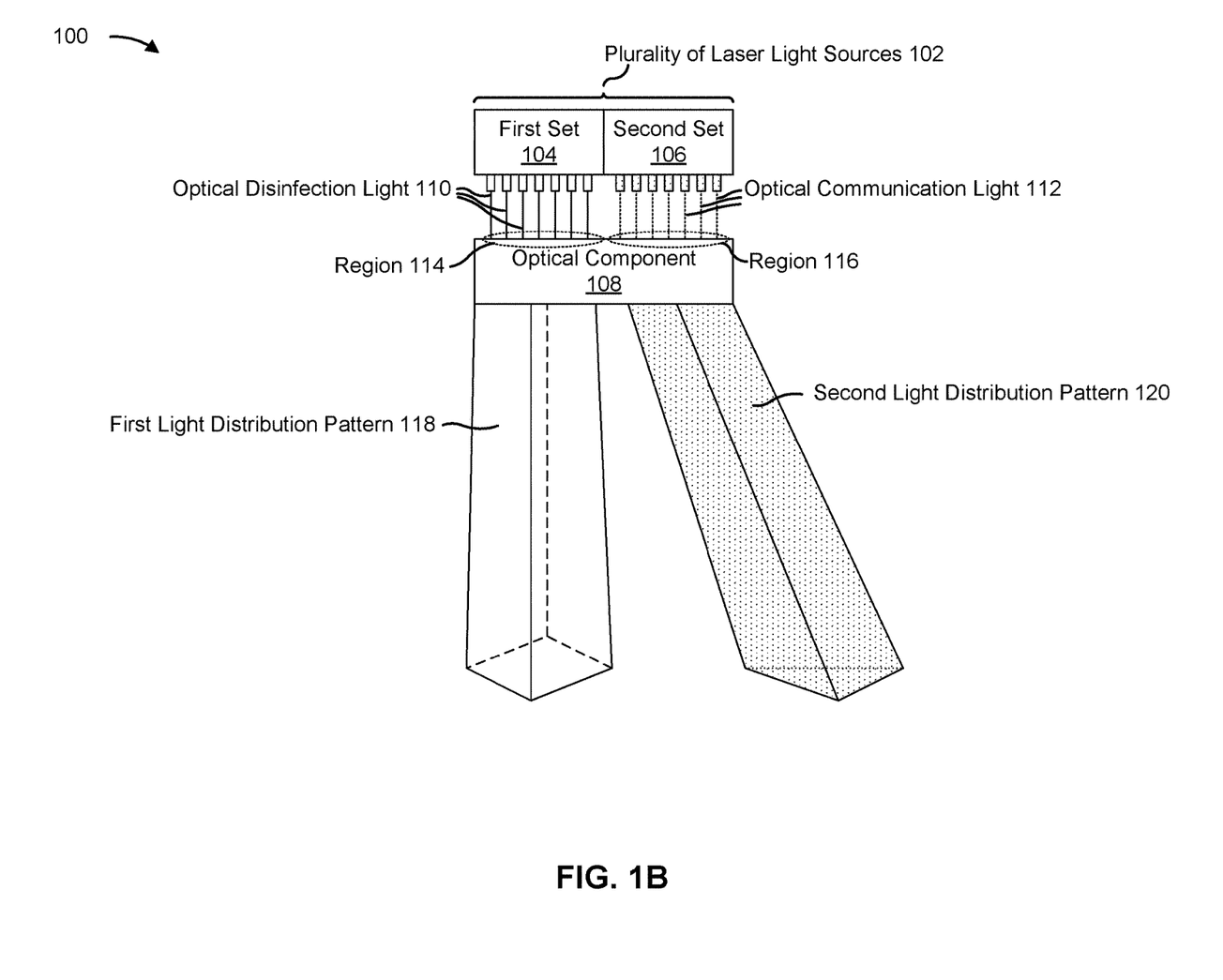
Figure 1C:
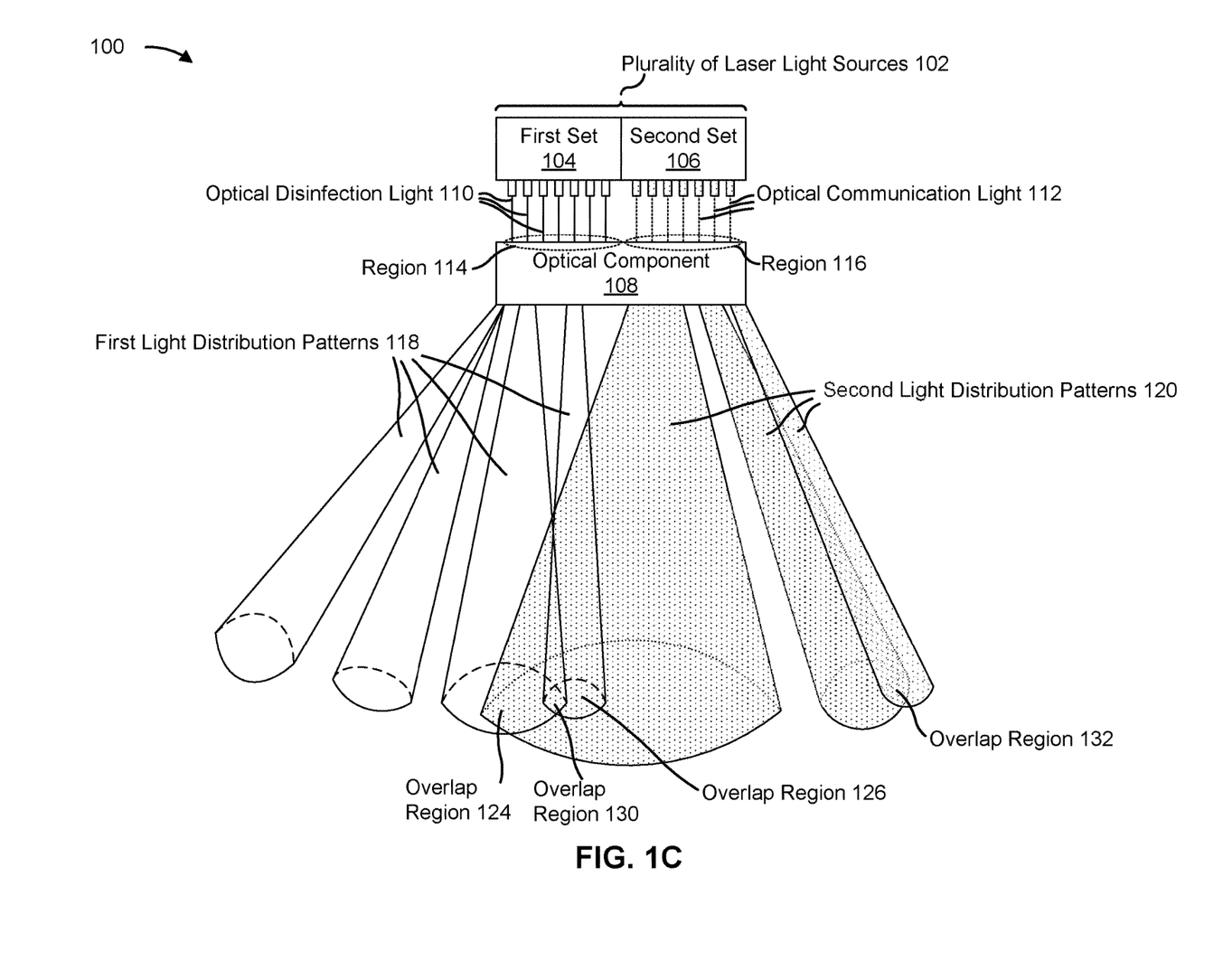

In some implementations, the first set of one or more laser light sources 104 may be configured to emit the optical disinfection light 110 at a region of a surface of the optical component 108. For example, as shown in FIGS. 1A-1C, the first set of one or more laser light sources 104 may be configured to emit the optical disinfection light 110 at a region 114 of a top surface of the optical component 108. Additionally, the second set of one or more laser light sources 106 may be configured to emit the optical communication light 112 at a region of a surface of the optical component 108. For example, as shown in FIGS. 1A-1C, the second set of one or more laser light sources 106 may be configured to emit the optical communication light 112 at a region 116 of a top surface of the optical component 108. As further shown in FIGS. 1A-1C, the region 114 and the region 116 may not overlap. That is, the first set of one or more laser light sources 104 may be configured to emit the optical disinfection light 110 at a first region of the surface of the optical component 108 that is different than a second region of the surface of the optical component 108 at which the second set of one or more laser light sources 106 are configured to emit the optical communication light 112.

Figure 1D:
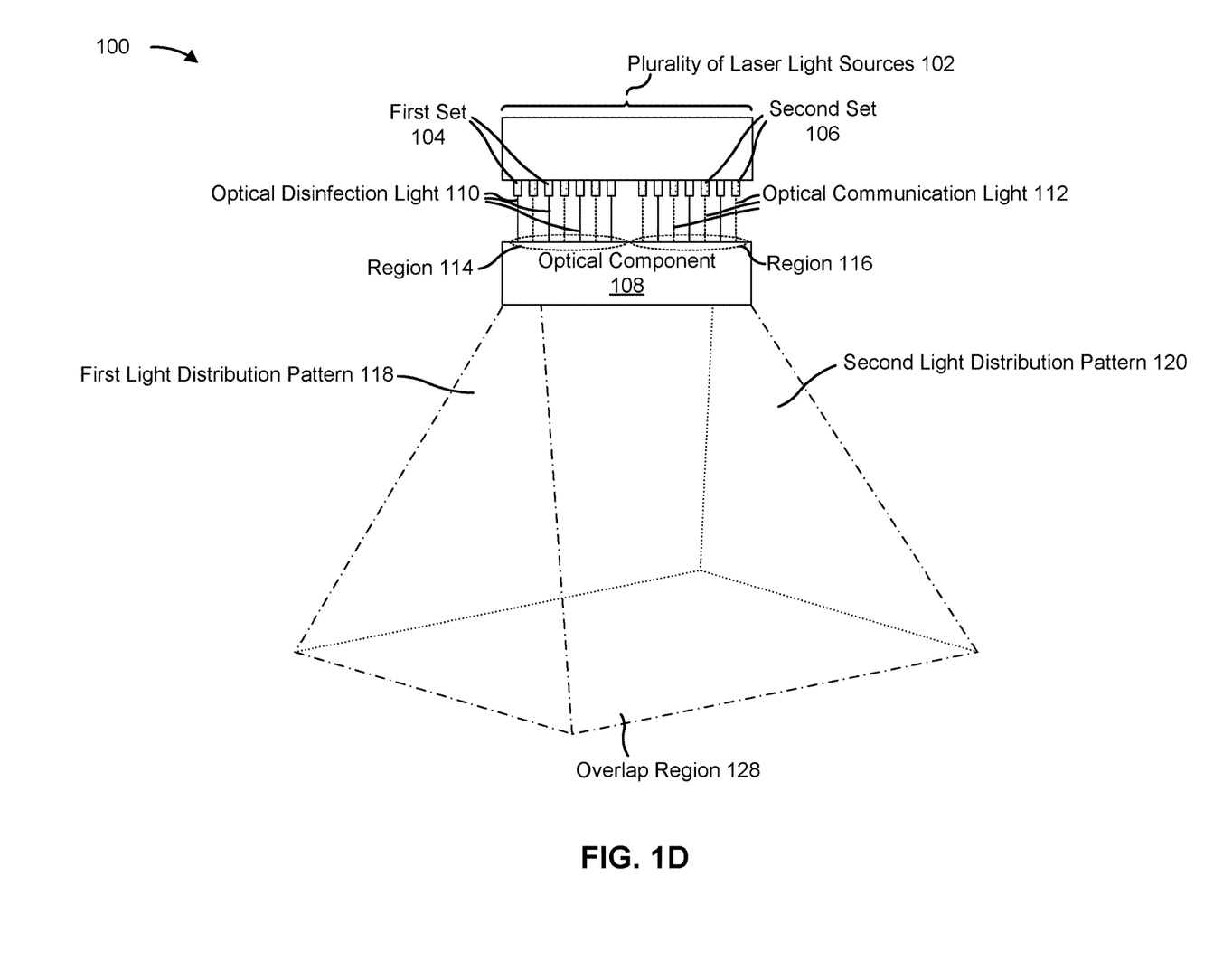

Alternatively, the first set of one or more laser light sources 104 may be configured to emit at least some of the optical disinfection light 110 at a region of a surface of the optical component 108, and the second set of one or more laser light sources 106 may be configured to emit at least some of the optical communication light 112 at the region (e.g., the same region) of the surface of the optical component 108. For example, as shown in FIG. 1D, the first set of one or more laser light sources 104 may be configured to emit at least some of the optical disinfection light 110 at the region 114 of the top surface of the optical component 108, and the second set of one or more laser light sources 106 may be configured to emit at least some of the optical communication light 112 at the region 114. As further shown in FIG. 1D, the first set of one or more laser light sources 104 may be configured to emit at least some of the optical disinfection light 110 at the region 116 of the top surface of the optical component 108, and the second set of one or more laser light sources 106 may be configured to emit at least some of the optical communication light 112 at the region 116.

The optical component 108 may be an optical diffuser (e.g., a structured optical diffuser, such as comprising fused silica) and/or may include one or more metamaterial structures. Further description of the optical component 108 is described herein in relation to FIGS. 2A-2B.

As shown in FIGS. 1A-1D, the optical component 108 may be configured to distribute the optical disinfection light 110 in one or more first light distribution patterns 118. Additionally, the optical component 108 may be configured to distribute the optical communication light 112 in one or more second light distribution patterns 120. For example, as shown in FIGS. 1A, 1B, and 1D, the optical component 108 may be configured to distribute the optical disinfection light 110 in a single first light distribution pattern 118 and may be configured to distribute the optical communication light 112 in a single second light distribution pattern 120. As another example, as shown in FIG. 1C, the optical component 108 may be configured to distribute the optical disinfection light 110 in a plurality of first light distribution patterns 118 and may be configured to distribute the optical communication light 112 in a plurality of second light distribution patterns 120.

In some implementations, respective cross-sections of the one or more first light distribution patterns 118 and the one or more second light distribution patterns 120 may have round shapes or polygonal shapes (e.g., respective cross-sections cut in a plane that is orthogonal to an emission direction of the optical disinfection light 110 from the first set of laser light sources 104 and/or an emission direction of the optical communication light 112 from the second set of laser light sources 106). For example, as shown in FIG. 1A, cross-sections of a first light distribution pattern 118 and of a second light distribution pattern 120 each have a round shape. As another example, as shown in FIG. 1B, cross-sections of a first light distribution pattern 118 and of a second light distribution pattern 120 each have a polygonal shape (e.g., a rectangular shape for the first light distribution pattern 118 and a triangular shape for the second light distribution pattern 120).

In some implementations, a cross-section of at least one first light distribution pattern 118, of the one or more first light distribution patterns 118, overlaps with a cross-section of at least one second light distribution pattern 120, of the one or more second light distribution patterns 120. For example, as shown in FIG. 1A, a cross-section of a first light distribution pattern 118 overlaps with a cross-section of a second light distribution pattern 120 at an overlap region 122. As another example, as shown in FIG. 1C, a cross-section of a second light distribution pattern 120 overlaps with a cross-section of a particular first light distribution pattern 118 at an overlap region 124, and overlaps with a cross-section of another particular first light distribution pattern 118 at an overlap region 126 (e.g., such that the cross-section of the other particular first light distribution pattern is fully within the cross-section of the second light distribution pattern 120). In another example, as shown in FIG. 1D, a cross-section of a first light distribution pattern 118 and a cross-section of a second light distribution pattern 120 fully overlap each other at an overlap region 128 (e.g., the respective cross-sections of the first light distribution pattern 118 and the second light distribution pattern 120 each have a polygonal shape and are co-extensive).

In some implementations, no cross-section of a first light distribution pattern 118, of the one or more first light distribution patterns 118, overlaps with a cross-section of a second light distribution pattern 120, of the one or more second light distribution patterns 120. For example, as shown in FIG. 1B, a cross-section of a first light distribution pattern 118 does not overlap with a cross-section of a second light distribution pattern 120.

In some implementations, respective cross-sections of at least two first light distribution patterns 118, when there are a plurality of first light distribution patterns 118, may overlap with each other. For example, as shown in FIG. 1C, respective cross-sections of a particular first light distribution 118 pattern, of the plurality of first light distribution patterns 118, and another particular first light distribution pattern 118, of the plurality of first light distribution patterns 118, overlap at an overlap region 130. In some implementations, respective cross-sections of at least two second light distribution patterns 120, when there are a plurality of second light distribution patterns 120, may overlap with each other. For example, as shown in FIG. 1C, respective cross-sections of a particular second light distribution 120 pattern, of the plurality of second light distribution patterns 120, and another particular second light distribution pattern 120, of the plurality of first light distribution patterns, overlap at an overlap region 132.

In some implementations, respective cross-sections of at least two first light distribution patterns 118, when there are a plurality of first light distribution patterns 118, may not overlap with each other, such as shown in FIG. 1C (e.g., the two left-most first light distribution patterns 118). In some implementations, respective cross-sections of at least two second light distribution patterns 120, when there are a plurality of second light distribution patterns 120, may not overlap with each other, such as shown in FIG. 1C (e.g., the left-most second light distribution pattern 120 and the right-most second light distribution pattern 120).

In some implementations, the optical component 108 may be configured to distribute the optical disinfection light 110 (e.g., in the one or more first light distribution patterns 118), such that a radiant exposure associated with the optical disinfection light 110 in the one or more first light distribution patterns 118 is less than or equal to a radiant exposure threshold. The radiant exposure threshold may be, for example, less than or equal to 1 millijoules per square centimeter per hour (mJ/cm$^2$/hr), 3 mJ/cm$^2$/hr, and/or 5 mJ/cm$^2$/hr. In this way, the optical disinfection light 110 may be distributed in a "dose" that is safe for human tissue (e.g., that may be exposed in the one or more first light distribution patterns 118).

As indicated above, FIGS. 1A-1D are provided as examples. Other examples may differ from what is described with regard to FIGS. 1A-1D.

Figure 2A:
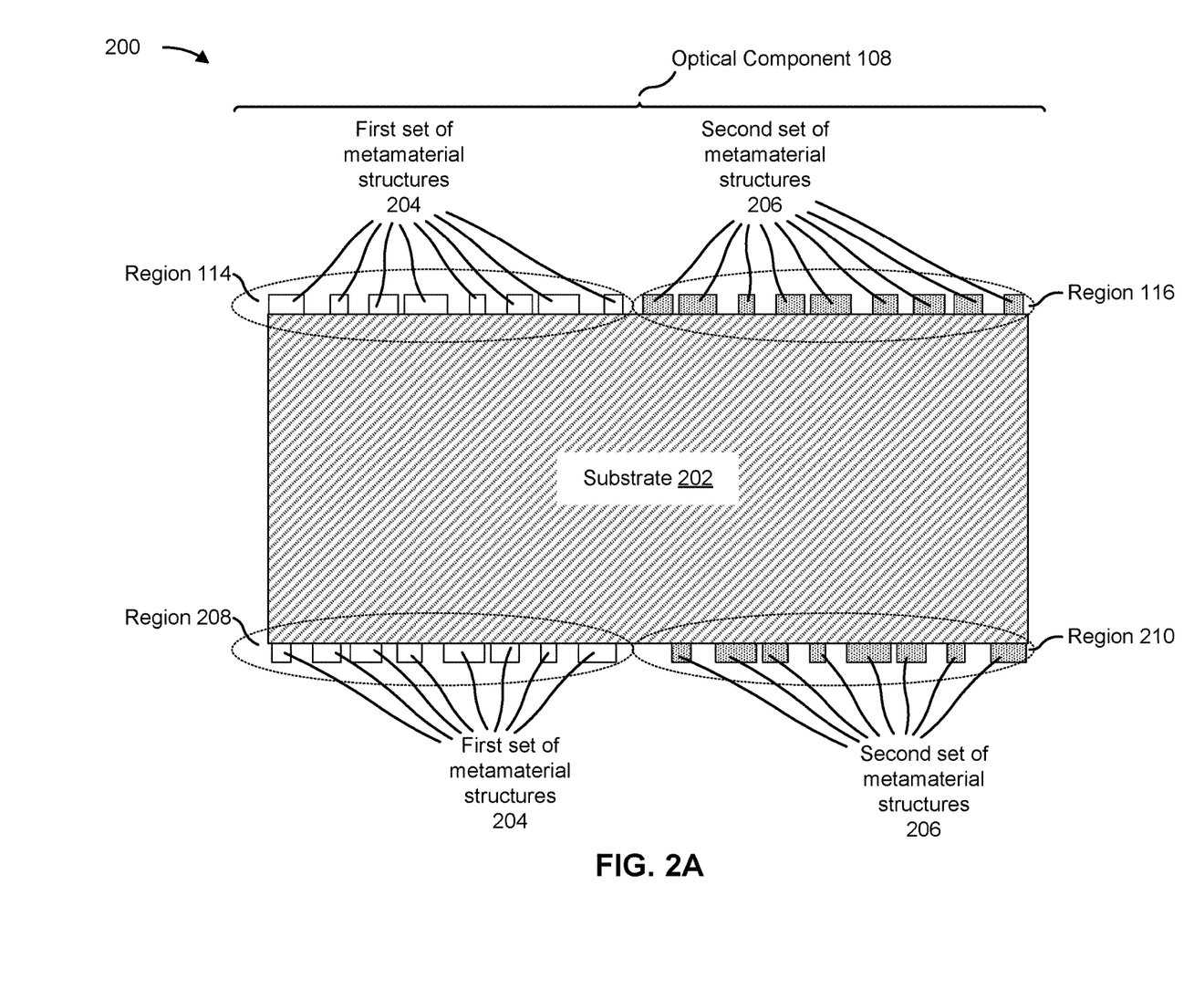
FIGS. 2A-2B are diagrams illustrating example implementations of an optical component described herein.
Figure 2B:
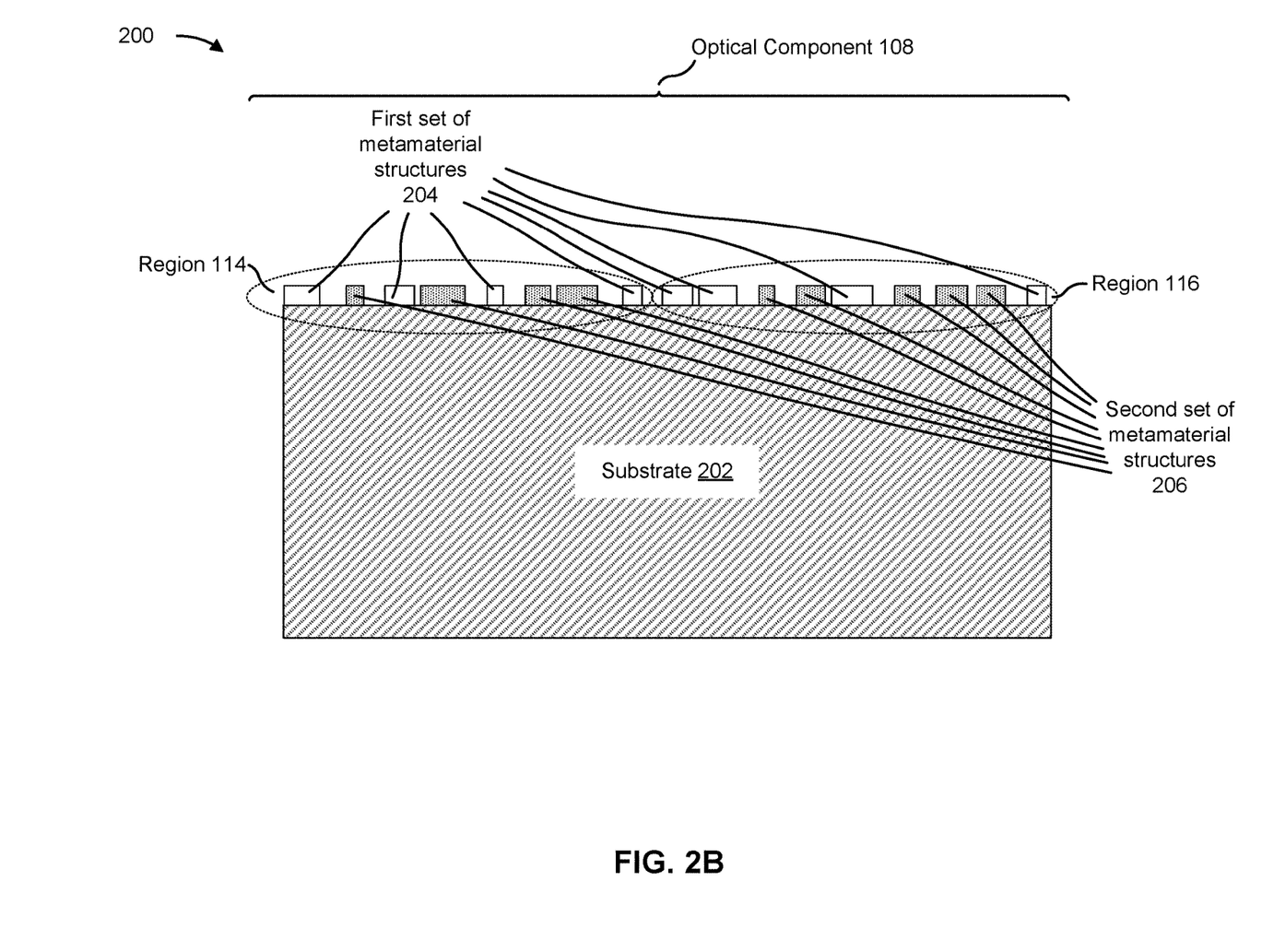

FIGS. 2A-2B are diagrams 200 illustrating example implementations of the optical component 108. As shown in FIGS. 2A-2B, the optical component 108 may include a substrate 202, a first set of one or more metamaterial structures 204, and/or a second set of one or more metamaterial structures 206.

The substrate 202 may be a glass substrate, a silicon substrate, a germanium substrate, or another type of substrate. The substrate 202 may be configured to transmit (e.g., through the substrate 202) at least a threshold percentage of each of the optical disinfection light 110 and the optical communication light 112. The threshold percentage may be, for example, greater than or equal to 75%, 85%, 90%, 95%, 99%, and/or 99.5%.

The substrate 202 may have one or more surfaces, such as a top surface, a bottom surface, and two side surfaces (e.g., a left side surface and a right side surface), as shown in FIGS. 2A-2B. The one or more surfaces of the substrate 202 may be equivalent to one or more surfaces of the optical component 108 (e.g., the one or more surfaces of the substrate 202 and the one or more surfaces of the optical component 108 may be the same). The first set of one or more metamaterial structures 204 may be disposed on at least one surface of the substrate 202 and the second set of one or more metamaterial structures 206 may be disposed on at least one surface of the substrate 202. Accordingly, at least one surface of the optical component 108 may include the first set of one or more metamaterial structures 204 and at least one surface of the optical component 108 may include the second set of one or more metamaterial structures 206.

For example, as shown in FIG. 2A, the first set of one or more metamaterial structures 204 may be disposed on the region 114 of the top surface of the optical component 108 (e.g., the top surface of the substrate 202) and/or may be disposed on a region 208 of a bottom surface of the optical component 108 (e.g., the bottom surface of the substrate 202). As further shown in FIG. 2A, the second set of one or more metamaterial structures 206 may be disposed on the region 116 of the top surface of the optical component 108 (e.g., the top surface of the substrate 202) and/or may be disposed on a region 210 of a bottom surface of the optical component 108 (e.g., the bottom surface of the substrate 202). Accordingly, at least some of the first set of one or more metamaterial structures 204 may be disposed on a region of a particular surface of the optical component 108, and none of the second set of one or more metamaterial structures 206 may be disposed on the region of the particular surface of the optical component 108, and vice-versa.

In some implementations, at least some of the first set of one or more metamaterial structures 204 and at least some of the second set of one or more metamaterial structures 206 may be disposed on a region (e.g., the same region) of a particular surface of the optical component 108 (e.g., a particular surface of the substrate 202). For example, as shown in FIG. 2B, at least some of the first set of one or more metamaterial structures 204 and at least some of the second set of one or more metamaterial structures 206 may be disposed on the region 114 of the top surface of the optical component 108 (e.g., the top surface of the substrate 202). As further shown in FIG. 2B, at least some of the first set of one or more metamaterial structures 204 and at least some of the second set of one or more metamaterial structures 206 may be disposed on the region 116 of the top surface of the optical component 108 (e.g., the top surface of the substrate 202).

In some implementations, the first set of one or more metamaterial structures 204 may be configured to distribute the optical disinfection light 110 in the one or more first light distribution patterns 118 (e.g., as described herein in relation to FIGS. 1A-1D). For example, the first set of one or more metamaterial structures 204 may be configured to distribute, in the one or more first light distribution patterns 118, the optical disinfection light 110 that is incident on the optical component 108 (e.g., after the optical disinfection light 110 is emitted by the first set of one or more laser light sources 104). In some implementations, the first set of one or more metamaterial structures 204 may be configured to not affect a propagation of the optical communication light 112 (e.g., that is incident on the optical component 108 after the optical communication light 112 is emitted by the second set of one or more laser light sources 106). In this way, the first set of one or more metamaterial structures 204 may be configured to distribute the optical disinfection light 110, and may be configured to not distribute the optical communication light 112.

In some implementations, each metamaterial structure 204 of the first set of one or more metamaterial structures 204 may be an engineered structure (e.g., with an engineered shape, size, geometry, and/or orientation, among other examples). Each metamaterial structure 204 may have dimensions (e.g., a height, width, and/or thickness) that are greater than or equal to 100 nm and less than or equal to a minimum value of a spectral range associated with the optical disinfection light 110. For example, each metamaterial structure 204 may have dimensions that are less than or equal to 200 nm, such as when the optical disinfection light 110 includes UVC light, or that are less than or equal to 207 nm, such as when the optical disinfection light 110 includes Far UVC light. In some implementations, the first set of one or more metamaterial structures 204 may be arranged in a pattern (e.g., a linear pattern, a non-linear pattern, a regular pattern, and/or a non-regular pattern), where a distance between any two metamaterial structures 204 is less than or equal to the minimum value of the spectral range associated with the optical disinfection light 110.

In some implementations, the first set of one or more metamaterial structures 204 may be configured to produce a phase delay in one or more portions of the optical disinfection light 110, such as when the optical disinfection light 110 propagates through the optical component 108 (e.g., through the substrate 202). This may thereby change a propagation direction of the one or more portions of the optical disinfection light 110 (e.g., cause the one or more portions of the optical disinfection light 110 to diffract, refract, or otherwise bend when propagating through the optical component 108) and cause the optical disinfection light 110 to be distributed in the one or more first light distribution patterns 118.

In some implementations, the second set of one or more metamaterial structures 206 may be configured to distribute the optical communication light 112 in the one or more second light distribution patterns 120 (e.g., as described herein in relation to FIGS. 1A-1D). For example, the second set of one or more metamaterial structures 206 may be configured to distribute, in the one or more second light distribution patterns 120, the optical communication light 112 that is incident on the optical component 108 (e.g., after the optical communication light 112 is emitted by the second set of one or more laser light sources 106). In some implementations, the second set of one or more metamaterial structures 206 may be configured to not affect a propagation of the optical disinfection light 110 (e.g., that is incident on the optical component 108 after the optical disinfection light 110 is emitted by the first set of one or more laser light sources 104). In this way, the second set of one or more metamaterial structures 206 may be configured to distribute the optical communication light 112, and may be configured to not distribute the optical disinfection light 110.

In some implementations, each metamaterial structure 206 of the second set of one or more metamaterial structures 206 may be an engineered structure (e.g., with an engineered shape, size, geometry, and/or orientation, among other examples). Each metamaterial structure 206 may have dimensions (e.g., a height, width, and/or thickness) that are greater than or equal to 100 nm and less than or equal to a minimum value of a spectral range associated with the optical communication light 112. For example, each metamaterial structure 206 may have dimensions that are less than or equal to 400 nm, such as when the optical communication light 112 includes visible light, or that are less than or equal to 780 nm, such as when the optical communication light 112 includes NIR light. In some implementations, each metamaterial structure 204 may have dimensions that are greater than the minimum value of the spectral range associated with the optical disinfection light 110 (e.g., greater than 200 nm when the optical disinfection light 110 includes UVC light or greater than 207 nm when the optical disinfection light 110 includes Far UVC light). In this way, any metamaterial structure 206, of the second set of one or more metamaterial structures 206, may have dimensions that are respectively greater than corresponding dimensions of any metamaterial structure 204, of the first set of one or more metamaterial structures 204. In some implementations, the second set of one or more metamaterial structures 206 may be arranged in a pattern (e.g., a linear pattern, a non-linear pattern, a regular pattern, and/or a non-regular pattern), where a distance between any two metamaterial structures 206 is less than or equal to the minimum value of the spectral range associated with the optical communication light 112.

In some implementations, the second set of one or more metamaterial structures 206 may be configured to produce a phase delay in one or more portions of the optical communication light 112, such as when the optical communication light 112 propagates through the optical component 108 (e.g., through the substrate 202). This may thereby change a propagation direction of the one or more portions of the optical communication light 112 (e.g., cause the one or more portions of the optical communication light 112 to diffract, refract, or otherwise bend when propagating through the optical component 108) and cause the optical communication light 112 to be distributed in the one or more second light distribution patterns 120.

As indicated above, FIGS. 2A-2B are provided as examples. Other examples may differ from what is described with regard to FIGS. 2A-2B.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of"). Further, spatially relative terms, such as "below," "lower," "bottom," "above," "upper," "top," and the like, may be used herein for ease of description to describe one element or feature's relationship to another element(s) or feature(s) as illustrated in the figures. The spatially relative terms are intended to encompass different orientations of the apparatus, device, and/or element in use or operation in addition to the orientation depicted in the figures. The apparatus may be otherwise oriented (rotated 90 degrees or at other orientations) and the spatially relative descriptors used herein may likewise be interpreted accordingly.

What is claimed is:

1. An optical system, comprising:
a plurality of laser light sources; and
an optical component, wherein:
a first set of one or more laser light sources, of the plurality of laser light sources, is configured to emit optical disinfection light at the optical component,
a second set of one or more laser light sources, of the plurality of laser light sources, is configured to emit optical communication light at the optical component, and
the optical component is configured to both distribute the optical disinfection light in a first light distribution pattern and distribute the optical communication light in a second light distribution pattern.

2. The optical system of claim 1, wherein:
the optical disinfection light includes light associated with a spectral range of 207 to 222 nanometers; and
the optical communication light includes light associated with a spectral range of 780 to 1399 nanometers.

3. The optical system of claim 1, wherein a surface of the optical component includes one or more metamaterial structures.

4. The optical system of claim 1, wherein the optical component is an optical diffuser.

5. The optical system of claim 1, wherein respective cross-sections of the first light distribution pattern and the second light distribution pattern have polygonal shapes.

6. The optical system of claim 1, wherein a cross-section of the first light distribution pattern overlaps with a cross-section of the second light distribution pattern.

7. The optical system of claim 1, wherein a cross-section of the first light distribution pattern does not overlap with a cross-section of the second light distribution pattern.

8. The optical system of claim 1, wherein the optical component is configured to distribute the optical disinfection light such that a radiant exposure associated with the optical disinfection light in the first light distribution pattern is less than or equal to 3 millijoules per square centimeter per hour (mJ/cm2/hr).

9. The optical system of claim 1, wherein:
the first set of one or more laser light sources is configured to emit the optical disinfection light at a first region of a surface of the optical component;
the second set of one or more laser light sources is configured to emit the optical communication light at a second region of the surface of the optical component; and
the first region and the second region do not overlap.

10. The optical system of claim 1, wherein:
the first set of one or more laser light sources is configured to emit at least some of the optical disinfection light at a region of a surface of the optical component; and
the second set of one or more laser light sources is configured to emit at least some of the optical communication light at the region of the surface of the optical component.

11. An optical system, comprising:
a plurality of laser light sources; and
an optical component, wherein:
a first set of one or more laser light sources, of the plurality of laser light sources, is configured to emit optical disinfection light at the optical component,
a second set of one or more laser light sources, of the plurality of laser light sources, is configured to emit optical communication light at the optical component, and
the optical component is configured to both distribute the optical disinfection light in a plurality of first light distribution patterns and distribute the optical communication light in a plurality of second light distribution patterns.

12. The optical system of claim 11, wherein:
the optical disinfection light includes light associated with a spectral range of 200 to 280 nanometers; and
the optical communication light includes light associated with a spectral range of 400 to 1399 nanometers.

13. The optical system of claim 11, wherein respective cross-sections of a particular first light distribution pattern, of the plurality of first light distribution patterns, and another particular first light distribution pattern, of the plurality of first light distribution patterns, overlap.

14. The optical system of claim 11, wherein a cross-section of at least one first light distribution pattern, of the plurality of first light distribution patterns, overlaps with a cross-section of at least one second light distribution pattern, of the plurality of second light distribution patterns.

15. The optical system of claim 11, wherein:
at least one surface of the optical component includes a first set of one or more metamaterial structures configured to distribute the optical disinfection light in the plurality of first light distribution patterns; and
at least one surface of the optical component includes a second set of one or more metamaterial structures configured to distribute the optical disinfection light in the plurality of second light distribution patterns.

16. An optical system, comprising:
a plurality of laser light sources including:
one or more first light sources configured to emit a first type of light, and
one or more second light sources configured to emit a second type of light; and
an optical component configured to both distribute the first type of light in a first light distribution pattern and distribute the second type of light in a second light distribution pattern.

17. The optical system of claim 16,
wherein the first type of light comprises optical disinfection light, and
wherein the second type of light comprises optical communication light.

18. The optical system of claim 16, wherein the optical component comprises:
a first set of one or more metamaterial structures disposed on at least one surface of the optical component, and
a second set of one or more metamaterial structures disposed on the at least one surface of the optical component.

19. The optical system of claim 18,
wherein the first set of one or more metamaterial structures are configured to distribute, in the first light distribution pattern, the first type of light, and
wherein the second set of one or more metamaterial structures are configured to distribute, in the second light distribution pattern, the second type of light.

20. The optical component of claim 18, wherein:
at least some of the first set of one or more metamaterial structures is disposed on a region of a particular surface of the optical component, and
none of the second set of one or more metamaterial structures are disposed on the region of the particular surface of the optical component.

* * * * *